United States Patent [19]

Myer

[11] 4,414,985

[45] Nov. 15, 1983

[54] OPHTHALMIC CLIP

[75] Inventor: Jon H. Myer, Woodland Hills, Calif.

[73] Assignee: Hughes Aircraft Company, El Segundo, Calif.

[21] Appl. No.: 385,356

[22] Filed: Jun. 7, 1982

Related U.S. Application Data

[62] Division of Ser. No. 137,682, Apr. 7, 1980.

[51] Int. Cl.$^3$ .............................................. A61B 5/10
[52] U.S. Cl. ................................... 128/782; 128/774; 128/321; 73/862.54; 24/501
[58] Field of Search ............... 128/774, 782, 321, 325, 128/327; 73/862.53, 862.54; 24/252 R, 137 R, 67.5

[56] References Cited

U.S. PATENT DOCUMENTS

| | | | |
|---|---|---|---|
| 2,205,379 | 6/1940 | Agostineto | 24/252 R |
| 2,252,798 | 8/1940 | Arnold | 73/862.52 X |
| 2,475,436 | 7/1949 | Roark | 24/252 R |
| 2,478,595 | 8/1949 | Richter | 128/321 |
| 2,596,456 | 5/1952 | Williams | 73/167 X |
| 3,326,217 | 6/1967 | Kerr | 24/252 R X |
| 3,393,680 | 7/1968 | Curutchet | 128/321 |
| 3,785,381 | 1/1974 | Lower et al. | 73/862.54 X |
| 3,797,498 | 3/1974 | Walsh et al. | 24/252 R X |

FOREIGN PATENT DOCUMENTS

| | | | |
|---|---|---|---|
| 199452 | 7/1967 | U.S.S.R. | 73/862.54 |
| 245409 | 6/1969 | U.S.S.R. | 73/862.53 |

OTHER PUBLICATIONS

Schillinger, "Prevention of Over-Correction and Under Correction in Horiz. Strabismus Surgery", *Journal of Ped. Ophth.*, vol. 3, No. 3, 1966, pp. 38-41.

Scott, "Extraocular Muscle Forces in Strabismus", *The Control of Eye Movements.*

Scott, "Active Force Tests in Lateral Rectus Paralysis", *Arch. Ophthal.*, vol. 85, 4/71, pp. 397-404.

Rosenbaum et al., "New Instrument for the Quantitative Determination of Passive Forced Traction", *Ophthalmology*, 2/80, vol. 87, No. 2, pp. 158-163.

Storz Instrument Co., Ophthalmic Surgical Instruments and Equipment, 12th Edition, 1980.

Scott et al., "A Forceps to Measure Strabismus Forces", Arch. Ophthal., vol. 88, 9/72, pp. 330-333.

Stephens et al., "Quantitative Forced Duction", Tr. Am. Acad. Ophth. and Otol., Mar.-Apr. 1967, pp. 324-329.

Storz Eye Instrument Catalog, Pierse-Type Forcep, 12th Edition, St. Louis: CV Mosby, 1977, 1978.

*Primary Examiner*—Kyle L. Howell
*Assistant Examiner*—Angela D. Sykes
*Attorney, Agent, or Firm*—Lewis B. Sternfels; William J. Bethurum; A. W. Karambelas

[57] ABSTRACT

Apparatus useful in the surgical correction of strabismus comprises a clip (10) attachable to the sclera (52) of an eye, and a dynamometer gauge (12) coupled to the clip to measure torques exerted on the muscle of the eye.

5 Claims, 5 Drawing Figures

OPHTHALMIC CLIP

This is a division of application Ser. No. 137,682, filed Apr. 7, 1980.

BACKGROUND OF THE INVENTION

1. Field of the Invention

The present invention relates to a clip and, in particular, to a reverse-action clip. It is particularly useful for attachment to the sclera of the human eyeball and the method of its use.

2. Description of the Prior Art and Other Background Considerations

In ophthalmic surgery, the correction of strabismus, which is the condition of being cross- or wall-eyed involves proven surgical procedures in which the lines of vision are aligned by shortening or lengthening certain selected eye muscles by truncating excess muscle or by re-attaching the muscle at a new location.

Such muscle shortening or lengthening presently relies extensively on the experience and skill of the ophthalmic surgeon who, in general, grips the eyeball with a forceps and, while maintaining the closing force to maintain the grip, must visually estimate the amount by which the muscle must be shortened or lengthened. As a result, under or overcompensation can occur.

SUMMARY OF THE INVENTION

The present invention was devised to eliminate such error by substituting precise measurement for estimation. The measurement includes use of a reverse-action clip which is attachable to the sclera or leathery outer coat of the eyeball so that the surgeon can measure both the torque exerted on the muscle of the eye and the distance or angular movement of the eye necessary to align the lines of vision of both eyes. From this data, he can calculate the amount by which the eye muscles are to be shortened or lengthened.

It is, therefore, an object of the invention to provide a novel reverse-action clip.

Another object is to provide a means and method for determining eye ball torque forces required for the alignment of the lines of vision.

Another object is to provide for a means and method by which the force-displacement characteristics of the eye may be measured.

Another object is to provide a means for positively gripping the sclera without harm thereto.

Other aims and objects as well as a more complete understanding of the present invention will appear from the following explanation of an exemplary embodiment and the accompanying drawings thereof.

DETAILED DESCRIPTION OF THE INVENTION

Figure 2:
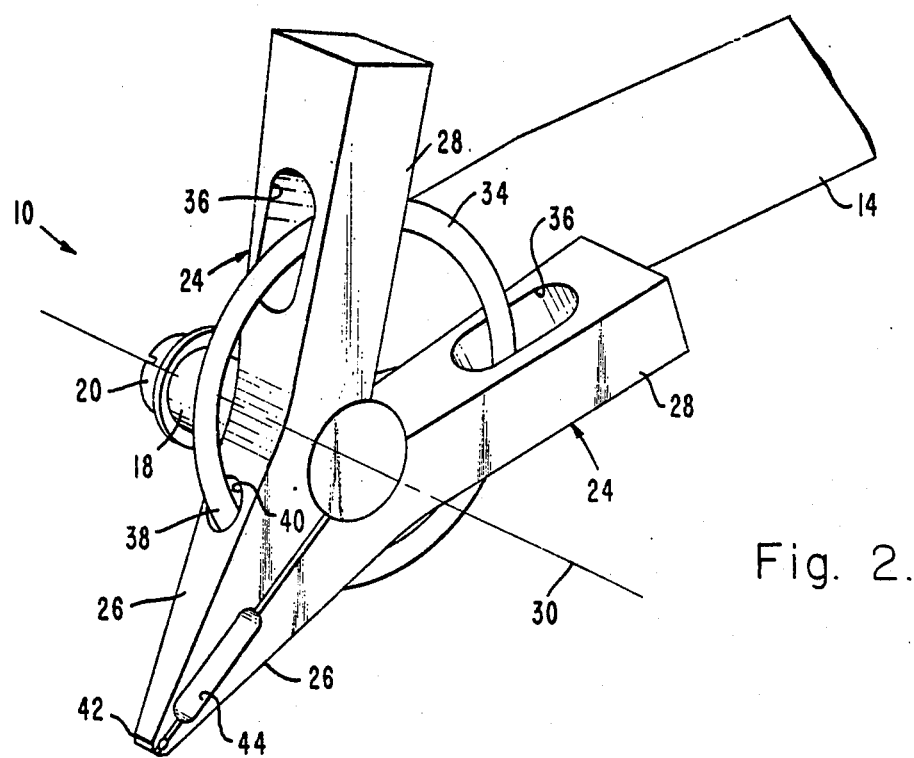
FIG. 2 is an enlarged perspective view of the clip shown in FIG. 1.
Figure 1:
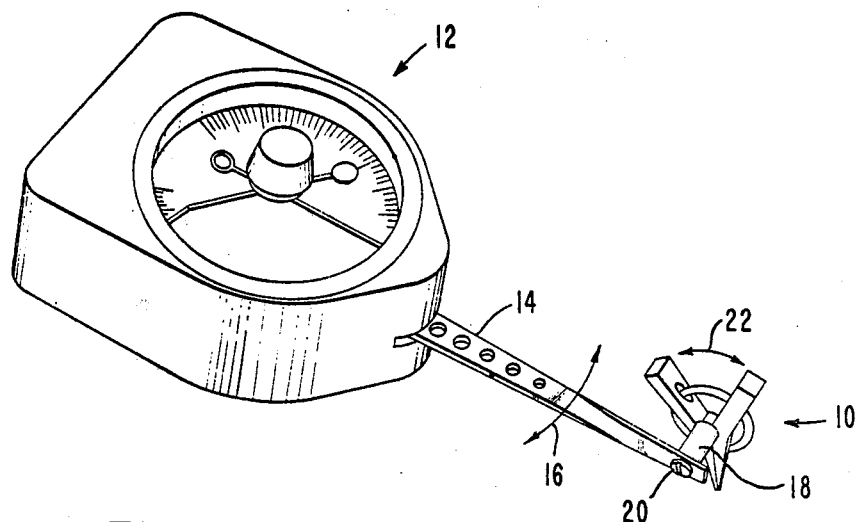
FIG. 1 is a perspective view of the preferred embodiment of the invention comprising a dynamometer force gage with a clip attached thereto.
Figure 3:
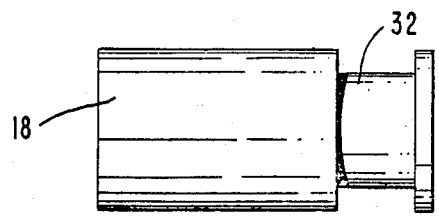
FIG. 3 is a view of the shaft forming the fulcrum of the clip depicted in FIG. 2.

Referring to FIGS. 1–3, a clip 10 is secured to a dynamometer gage 12 by means of an arm 14 extending from the gage. Gage 12 comprises a commercially available spring dynamometer force gage whose arm 14 is disposed to move or pivot in an arc 16 which lies in a single plane. Clip 10 is secured to arm 14 at a pivot in any convenient manner, such as by a screw 20 threaded into a shaft 18. Clip 10 is constrained to pivot in an arc 22 which also lies in a single plane. The planes of arcs 16 and 22 are normal to one another so that the swivel joint will isolate the desired force vector in the plane of arc 16, or in a plane parallel thereto, from any undesirable orthogonal forces in the plane of arc 22 during measurement.

As best shown in FIG. 2, clip 10 comprises a pair of levers 24, each having a jaw 26 and an extension 28. The points where extensions 28 angle from their jaws 26 combine to form a pivot axis 30 or fulcrum about which clip 10 can be opened or closed. This fulcrum is defined by an annular recess 32 in shaft 18 as shown in FIG. 3.

Levers 24 are spring biased to normally close jaws 26. Such spring loading is effected by a spring ring 34 which passes through apertures 36 in extensions 28 and engage at their ends 38 within recesses 40 in jaws 26.

Jaws 26 can be shaped in any desired configuration; however, it was found that the least grip on the sclera was obtained when the jaws were configured in the profile of a Pierse-type forceps 42. For additional reliability and to limit the possible interference of debris, the jaws are relieved between the Pierse-type forceps and the fulcrum. Preferably, spring ring 34 should exert a force of 2.5 to 3 newtons at the jaw tip, representing a compromise between clamping efficiency and minimum tissue damage.

Figure 4:
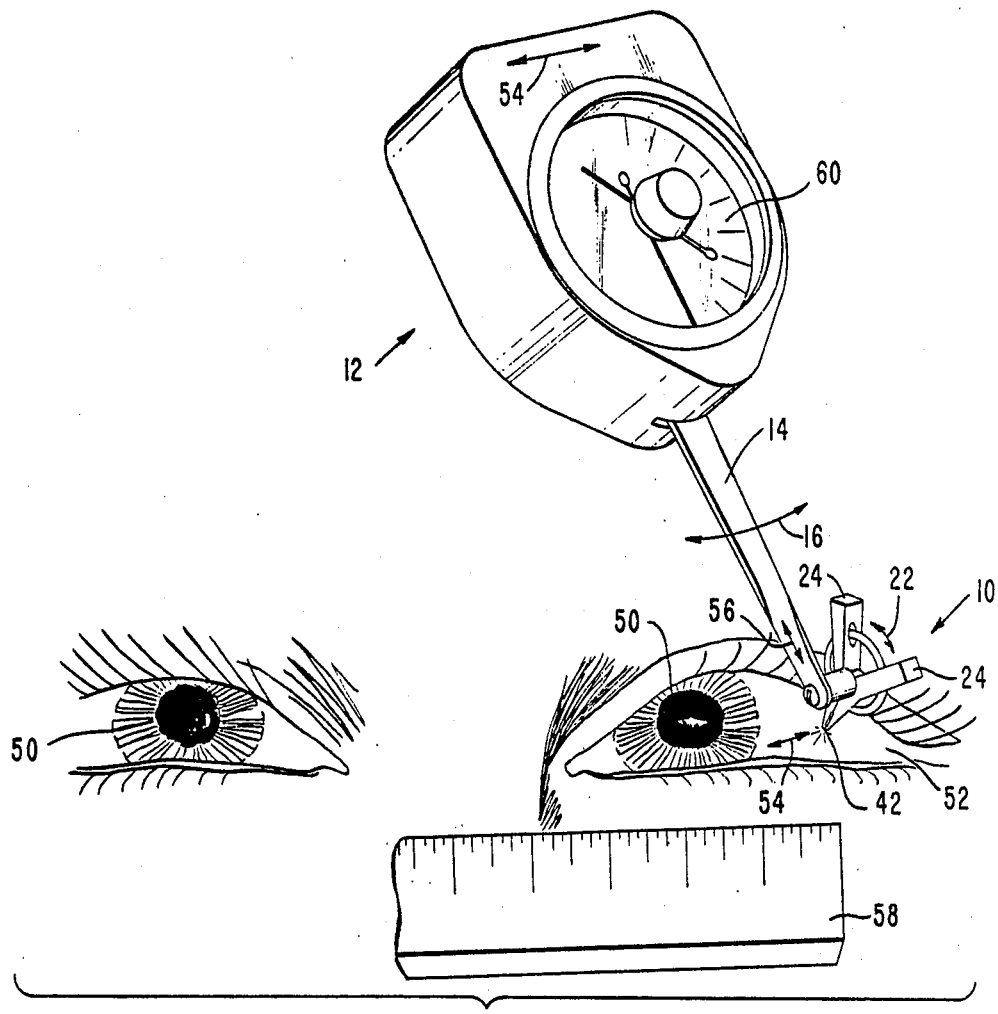
FIG. 4 is a view illustrating use of the present invention.
Figure 5:
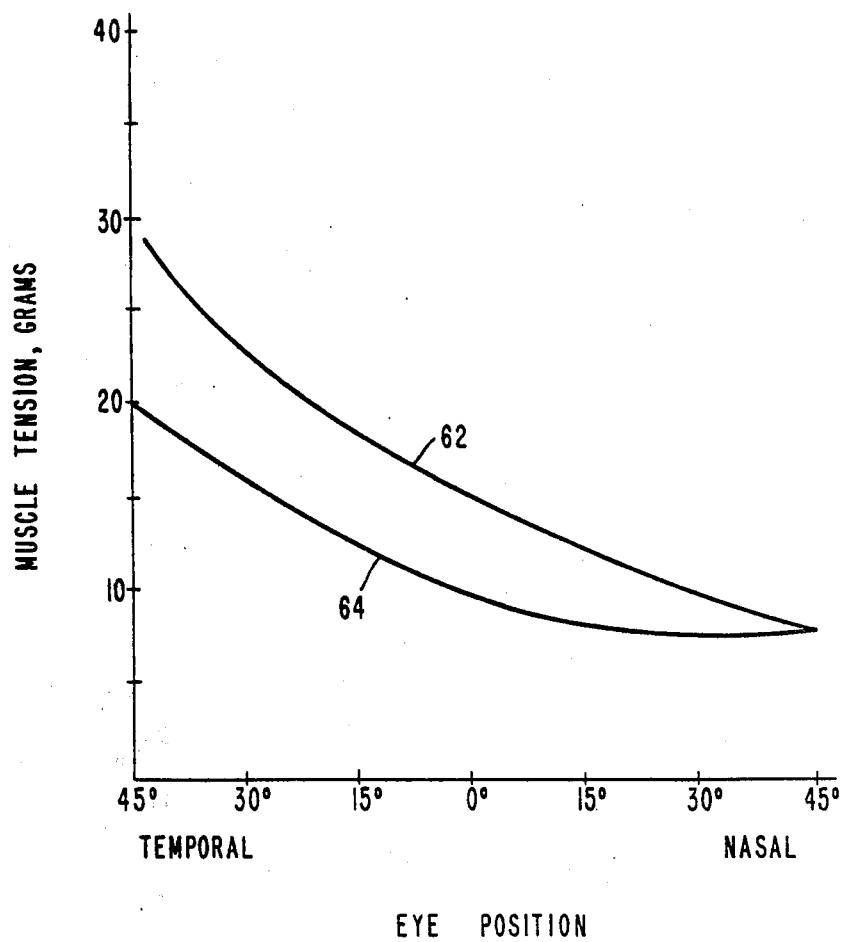
FIG. 5 is a graph of muscle tension versus eye position with respect to the ear and the nose of the patient, useful in determining the precise amount of muscle shortening required for the alignment of the lines of vision of the two eyes.

Use of the invention is illustrated with reference to FIGS. 4 and 5. In FIG. 4, a patient's eyes 50 are illustrated as exhibiting a cross-eyed or strabismus condition. To determine the necessary strabismus correction, the misalignment of the lines of vision of the eyes and the degree of torque required to provide alignment must be measured. The surgeon obtains such data by gripping the sclera or leathery outer coat 52 of the eyeball with clip 10 by pinching the sclera with the jaws of the clip. As result of the fulcrum design of clip 10, only the forces along line 54 are transmitted to arm 14, but not any forces along line 56. This isolation of the forces assures that only the desired force vector 54 is measured by the instrument as shown by arc 16. Any hand motion of the surgeon along line 56 is isolated by the free swivel action of clip 10 shown by arc 22.

After properly attaching the clip to the sclera, the surgeon then moves dynamometer gage 12 in the direction along line 54 necessary while monitoring the eye displacement. The distance over which the eye moves is determined by a ruler 58, for example. Such distance may be measured in linear millimeters or in angular degrees by placing the ruler at the eyeball and then by pulling the eye towards the nose or towards the ear, that is, respectively in a nasal or a temporal direction. While the eyeball is thus moved, it also creates a restoring force which is indicative of the muscle tension and is shown on the scale 60 of dynamometer gage 12. On the basis of these measurements and by comparing the resultant force-displacement data with data obtained from normal (non-strabismic) eyes, the surgeon can quantitatively determine the cause of the cross-eyed or wall-eyed condition, and can initiate the the applicable surgical procedure to correct the deficiency. Typical force-displacement data are plotted in the graph depicted in FIG. 5. There, muscle tension in grams for each eye is plotted versus its position, where the eye position is denoted in degrees in the temporal or nasal direction, as denoted. Here, for illustrative purposes, the difference in measurements between the two eyes is depicted by two curves, 62 and 64. The surgeon can then determine the amount and location of the muscle of the eye which must be shortened or lengthened to correct the strabismus.

Use of the combined clip and dynamometer gage also provides information as to possible other ophthalmic abnormalities. For example, a severe nonlinearity in the force-displacement curve, as shown by the torque readings on the dynamometer gage, may indicate the possible existence of a tumor, which obstructs free movement of the eyeball and presents an impediment or hump which temporarily impedes the motion of the eye as it is pulled by the combined dynamometer gage and clip.

Although the invention has been described with reference to a particular embodiment thereof, it should be realized that various changes and modifications may be made therein without departing from the spirit and scope of the invention.

What is claimed is:

1. A method for measuring torque on an eyeball to correct a strabismus condition, comprising the steps of:
displacing the eyeball in a single plane by means gripping the eyeball's sclera to exert a force on the eyeball sufficient to correct the condition while isolating any forces outside the single plane from being exerted on the eyeball; and
simultaneously with said displacing step, measuring the force exerted on the eyeball.

2. A method according to claim 1 further including the step of utilizing a reverse-action clip as the gripping means.

3. A method according to claims 1 or 2 further including the step of utilizing a Pierse-type forceps tip in said gripping means.

4. A method according to claim 1 wherein said measuring step includes the steps of attaching the gripping means to a force gage and transmitting only nasal and temporal displacements of the eyeball to the force gage.

5. A method according to claim 4 in which the force gage has an arm moveable in the single plane and wherein said transmitting step includes the step of moving the force gage arm generally parallel to the nasal and temporal displacements and pivoting the gripping means to the force gage arm for moving the gripping means in the single plane which is orthogonal to the plane in which the arm moves.

* * * * *